(12) United States Patent
Kobayashi et al.

(10) Patent No.: US 8,175,669 B2
(45) Date of Patent: May 8, 2012

(54) APPARATUS AND METHOD FOR MEASURING OXYGEN SATURATION IN BLOOD

(75) Inventors: Naoki Kobayashi, Tokyo (JP); Kenji Miyata, Tokyo (JP); Masaru Yarita, Tokyo (JP); Kazumasa Ito, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1411 days.

(21) Appl. No.: 11/508,995

(22) Filed: Aug. 24, 2006

(65) Prior Publication Data

US 2007/0049811 A1 Mar. 1, 2007

(30) Foreign Application Priority Data

Aug. 24, 2005 (JP) ............... P2005-242574
Jul. 28, 2006 (JP) ............... P2006-205453

(51) Int. Cl.
  *A61B 5/1455* (2006.01)
(52) U.S. Cl. ............... 600/336; 600/324
(58) Field of Classification Search ........... 600/309–344
  See application file for complete search history.

(56) References Cited

U.S. PATENT DOCUMENTS

| | | | |
|---|---|---|---|
| 4,934,372 A | 6/1990 | Corenman et al. | |
| 5,632,272 A | 5/1997 | Diab et al. | |
| 6,094,592 A | 7/2000 | Yorkey et al. | |
| 6,650,917 B2 | 11/2003 | Diab et al. | |
| 6,745,060 B2 | 6/2004 | Diab et al. | |
| 2004/0059209 A1 | 3/2004 | Al-Ali et al. | |
| 2004/0267140 A1 | 12/2004 | Ito et al. | |
| 2005/0033129 A1 | 2/2005 | Edgar, Jr. et al. | |

FOREIGN PATENT DOCUMENTS

| | | |
|---|---|---|
| JP | 3270917 B | 1/2002 |
| JP | 2003-024386 A | 1/2003 |
| JP | 2003-135434 A | 5/2003 |
| JP | 2005-95581 A | 4/2005 |
| JP | 2005-245574 A | 9/2005 |

OTHER PUBLICATIONS

Notification of Reasons for Refusal issued Apr. 26, 2011 in counterpart Japanese Application No. 2006-205453.

*Primary Examiner* — Eric Winakur
*Assistant Examiner* — Marjan Fardanesh
(74) *Attorney, Agent, or Firm* — Sughrue Mion, PLLC (57) ABSTRACT

In an apparatus for measuring an oxygen saturation in blood, a plurality of light emitters irradiate a living tissue with a plurality of light beams having different wavelengths. A light receiver receives the light beams reflected from or transmitted through the living tissue to generate pulse wave signals in accordance with pulsations of the blood in the living tissue. A separator separates each of the pulse wave signals into a plurality of amplitude signals each of which is associated with one frequency, thereby generating pairs of amplitude signals each of which is associated with one of a plurality of frequencies. A first processor calculates a ratio between the amplitude signals in each of the pairs of the amplitude signals. A selector selects one of the pairs of the amplitude signals. A second processor calculates the oxygen saturation from the ratio of the selected pair of the amplitude signals.

25 Claims, 8 Drawing Sheets

APPARATUS AND METHOD FOR MEASURING OXYGEN SATURATION IN BLOOD

BACKGROUND OF THE INVENTION

The present invention relates to signal processing in a pulse oximeter used in a patient monitoring or for diagnosing a respiratory system or a circulatory system.

Various methods have been proposed to separate a signal component and a noise component from two signals substantially simultaneously extracted from a single medium. The methods are usually conducted by performing processing in a frequency region and a time region.

In medical fields, it is known a pulse photometer including: an apparatus called a photoplethysmograph for measuring a pulse waveform and a pulse rate; and an apparatus for measuring the concentration of a light absorbing material in blood such as an apparatus for measuring an oxygen saturation in blood ($SpO_2$), an apparatus for measuring the concentration of abnormal hemoglobins such as carboxyhemoglobin and methemoglobin, and an apparatus for measuring the concentration of an injected dye. Particularly, the apparatus for measuring the $SpO_2$ is called a pulse oximeter.

The principle of the pulse photometer is to determine the concentration of an object material from a pulse wave signal obtained by causing a living tissue to transmit or reflect light beams, which have a plurality of wavelengths respectively correspond to different absorbances of the object material, and by continuously measuring an intensity of transmitted or reflected light. In a case where noise are superimposed on pulse wave data, calculation of a correct concentration or pulse rate cannot be achieved. Consequently, there is an anxious that an erroneous treatment may be performed.

There is proposed a method performed in the pulse photometer, in which pulse wave signals are divided into a plurality of frequency bands and a correlation between the signals is examined in each of the divided frequency bands to reduce noises. However, this method has a problem in that analysis is time-consuming.

Japanese Patent No. 3270917 discloses a method comprising: irradiating light beams respectively having different wavelengths onto a living tissue; drawing a graph in which the longitudinal axis and the transverse axis thereof respectively represent the magnitudes of two signals obtained from transmitted light; and obtaining a regression line to thereby obtain an oxygen saturation or the concentration of a light absorbing material in arterial blood according to the gradient of the regression line.

However, a large amount of calculation is needed to obtain a regression line and the gradient thereof by using a great amount of sampling-data on each of the pulse wave signals.

Japanese Patent Publication No. 2003-135434A discloses a method of using frequency analysis, in which the fundamental frequency of a pulse wave signal is obtained instead of conventional extraction of the pulse wave signal itself, and the pulse wave signal is filtered by using a filter employing a higher harmonic wave frequency to enhance accuracy. Japanese Patent Publication Nos. 2005-95581A and 2005-245574A disclose a method for separating noise from a pulse wave signal.

However, in a case where noise due to a body movement of a patient, whose amplitude is about ten times that of the pulse wave, is superimposed on a pulse wave signal, it is difficult according to any of these methods to compute a pulse rate and an oxygen saturation in arterial blood. Thus, a further improvement in signal processing is desired.

SUMMARY OF THE INVENTION

It is therefore an object of the invention to provide a signal processing method enabled to alleviate load calculation for extracting a common signal component by processing two signals of a same kind, which are substantially simultaneously extracted from a same medium.

It is also an object of the invention to measure the oxygen saturation of an object material with high accuracy by applying the signal processing method even when noise due to the body movement of the medium is superimposed on a pulse wave signal, thereby obtaining a pulse rate with high precision.

In order to achieve the above objects, according to the invention, there is provided an apparatus for measuring an oxygen saturation in blood, comprising:

a plurality of light emitters, adapted to irradiate a living tissue with a plurality of light beams having different wavelengths;

a light receiver, adapted to receive the light beams reflected from or transmitted through the living tissue to generate pulse wave signals in accordance with pulsations of the blood in the living tissue;

a separator, operable to separate each of the pulse wave signals into a plurality of amplitude signals each of which is associated with one frequency, thereby generating pairs of amplitude signals each of which is associated with one of a plurality of frequencies;

a first processor, operable to calculate a ratio between the amplitude signals in each of the pairs of the amplitude signals;

a selector, operable to select one of the pairs of the amplitude signals; and a second processor, operable to calculate the oxygen saturation based on the ratio of the selected one of the pairs of the amplitude signals.

The separator may comprise either an FFT processor or a digital filter.

The selector may be operable to select such a pair of the amplitude signals that have maximum amplitude values.

The selector may be operable to select such a pair of the amplitude signals that the ratio takes a minimum value.

The first processor may comprise: a first calculator, operable to define a plurality of frequency bands each of which includes a plurality of amplitude signals obtained from each of the pulse wave signals, and operable to calculate an average value of the amplitude signals in each of the frequency bands, thereby generating pairs of average values each of which is associated with one of the frequency bands; and a second calculator, operable to calculate an average ratio between the average values in each of the pairs of the average values. The selector may be operable to select such a frequency band that the average ratio takes a minimum value.

The apparatus first processor may comprise: a first calculator, operable to: define a plurality of frequency bands each of which includes a plurality of amplitude signals obtained from each of the pulse wave signals; judge whether there is a maximal point of the amplitude signals in each of the frequency bands; and calculate an average value of the amplitude signals in at least one of the frequency bands which is judged as one including the maximal point, thereby at least one pair of average values each of which is associated with one of the frequency bands; and a second calculator, operable to calculate an average ratio between the average values in each of the at least one pair of the average values. The selector may be operable to select such a frequency band that the average ratio takes a minimum value.

The first processor may comprise: a first calculator, operable to calculate ratios each of which is a ratio between each of the pairs of the amplitude signals; and a second calculator, operable to define a plurality of frequency bands each of which includes a plurality of amplitude signals obtained from each of the pulse wave signals, and operable to calculate an average value of the ratios In each of the frequency bands, thereby generating a plurality of average values. The selector may be operable to select such a frequency band that the average value takes a minimum value.

A part of one of the frequency bands may be overlapped with a part of another one of the frequency bands.

The selector may be operable to select either such a pair of the amplitude signals that have maximum amplitude values or such a pair of the amplitude signals that the ratio takes a minimum value in accordance with a prescribed condition.

The prescribed condition may include a waveform of the amplitude signals.

The light beams may include a red light beam and an infrared light beam.

According to the invention, there is also provided a method for measuring an oxygen saturation in blood, comprising:

irradiating a living tissue with a plurality of light beams having different wavelengths;

receiving the light beams reflected from or transmitted through the living tissue to generate pulse wave signals in accordance with pulsations of the blood in the living tissue;

separating each of the pulse wave signals into a plurality of amplitude signals each of which is associated with one frequency, thereby generating pairs of amplitude signals each of which is associated with one of a plurality of frequencies;

calculating a ratio between the amplitude signals in each of the pairs of the amplitude signals;

selecting one of the pairs of the amplitude signals; and calculating the oxygen saturation based on the ratio of the selected one of the pairs of the amplitude signals.

The separating may be performed with either an FFT processing or a digital filtering.

Such a pair of the amplitude signals that have maximum amplitude values may be selected as the one of the pairs of the amplitude signals.

Such a pair of the amplitude signals that the ratio takes a minimum value may be selected as the one of the pairs of the amplitude signals.

The method may further comprise:

defining a plurality of frequency bands each of which includes a plurality of amplitude signals obtained from each of the pulse wave signals;

calculating an average value of the amplitude signals in each of the frequency bands, thereby generating pairs of average values each of which is associated with one of the frequency bands;

calculating an average ratio between the average values in each of the pairs of the average values; and selecting such a frequency band that the average ratio takes a minimum value.

The method may further comprise:

defining a plurality of frequency bands each of which includes a plurality of amplitude signals obtained from each of the pulse wave signals;

judging whether there is a maximal point of the amplitude signals in each of the frequency bands;

calculating an average value of the amplitude signals in at least one of the frequency bands which is judged as one including the maximal point, thereby at least one pair of average values each of which is associated with one of the frequency bands;

calculating an average ratio between the average values in each of the at least one pair of the average values; and selecting such a frequency band that the average ratio takes a minimum value.

The method may further comprise:

calculating ratios each of which is a ratio between each of the pairs of the amplitude signals;

defining a plurality of frequency bands each of which includes a plurality of amplitude signals obtained from each of the pulse wave signals;

calculating an average value of the ratios in each of the frequency bands, thereby generating a plurality of average values; and selecting such a frequency band that the average value takes a minimum value.

A part of one of the frequency bands may be overlapped with a part of another one of the frequency bands.

Either such a pair of the amplitude signals that have maximum amplitude values or such a pair of the amplitude signals that the ratio takes a minimum value may be selected as the one of the pairs of the amplitude signals in accordance with a prescribed condition.

The prescribed condition may include a waveform of the amplitude signals.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Embodiments of the invention will be described below in detail with reference to the accompanying drawings.

Figure 1:
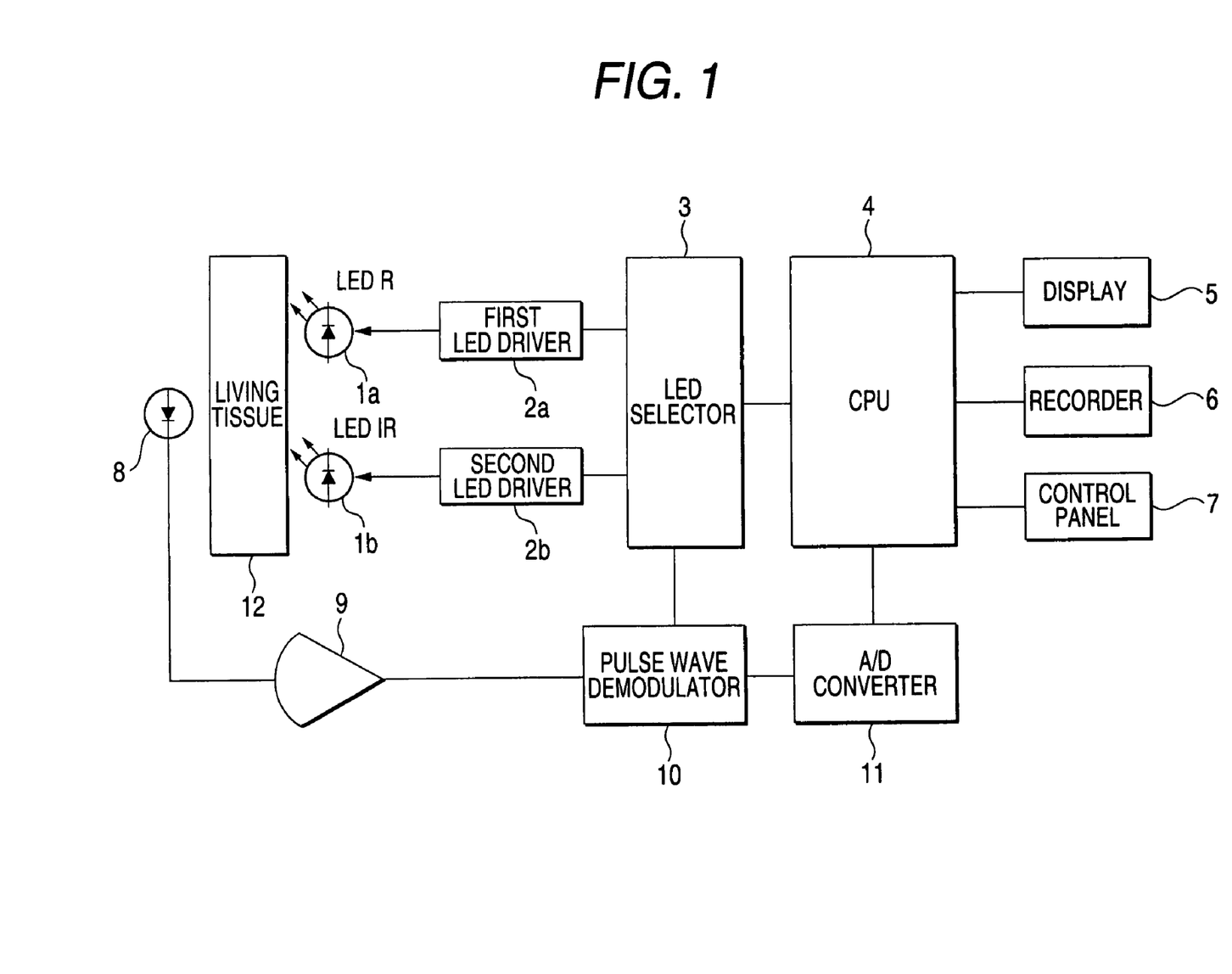
FIG. 1 is a block diagram schematically showing a pulse oximeter.

As shown in FIG. 1, in a pulse oximeter of the invention, light emitters 1a (LED R) and 1b (LED IR) are driven by a first LED driver 2a, a second LED driver 2b and an LED selector 3 to alternately emit light.

Preferably, light emitted from the light emitter 1a is red light (for example, the wavelength is 660 nm), which is highly sensitive to change in the oxygen saturation in arterial blood, and light emitted from the light emitter 1b is infrared light (for example, the wavelength is 940 nm), which is less sensitive to the change in the oxygen saturation in arterial blood.

Light beams coming from these light emitters 1a and 1b are transmitted (or reflected) by a living tissue 12 and are subsequently received by a photodiode 8 that converts the received light to photoelectric current. Then, a current-voltage converter 9 converts the photoelectric current to a voltage signal that is outputted to an A/D converter 11 through a pulse wave demodulator 10.

An LED selection signal is applied from the LED selector 3 to the pulse wave demodulator 10 as a timing signal. Thus, the red light and the infrared light received by the single photodiode 8 are extracted as separate pulse wave signals.

Pulse wave signals digitalized by the A/D converter 11 are processed by a CPU (adapted to perform computing, processing, and control). The digital pulse wave signals are displayed on a display 5 and are recorded in a recorder 6.

A control panel 7 is operative to perform the setting for performing processing in the CPU.

Each of pulse waves respectively corresponding to red light R and infrared light IR is separated into an AC component and a DC component by filtering. In addition, the ratio AC/DC of the magnitude of the AC component to that of the DC component is calculated corresponding to each of the pulse waves R and IR to thereby calculate signals representing attenuation changes $\Delta A$.

The magnitude of the AC component in the pulse wave for the red light R is denoted as $R\_AC(t)$. The magnitude of the DC component in the pulse wave for the red light R is denoted as $R\_DC(t)$. The magnitude of the AC component in the pulse wave for the Infrared light IR is denoted as $IR\_AC(t)$. The magnitude of the DC component in the pulse wave for the infrared light IR is denoted as $IR\_DC(t)$.

Figure 2A:
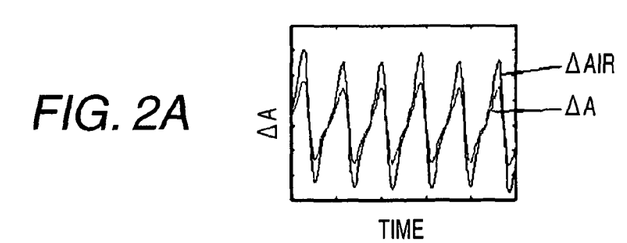
FIG. 2A is a graph showing attenuation change signals obtained from pulse wave signals measured by the pulse oximeter, in a case where no noise is superimposed.

Thus, the attenuation change signal for the red light R is expressed by $\Delta Ar(t)=R\_AC(t)/R\_DC(t)$, and the attenuation change signal for the infrared light IR is expressed by $\Delta Air(t)=IR\_AC(t)/IR\_DC(t)$. FIG. 2A shows these attenuation change signals.

Figure 2B:
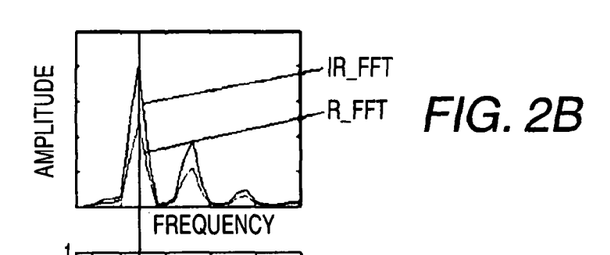
FIG. 2B is a graph showing amplitude spectra obtained by applying a FFT processing with respect to the pulse wave signals shown in FIG. 2A.

FIG. 2B shows amplitude spectra obtained after FFT processing is performed on the pulse waves shown in FIG. 2A. The amplitude spectrum corresponding to $\Delta Ar(t)$ is denoted as $R\_FFT(f)$, and the amplitude spectrum corresponding to $\Delta Air(t)$ is denoted as $IR\_FFT(f)$. Because no noise are superimposed on the pulse waves, each of the amplitude spectra shows a maximum value at a frequency of the pulse wave.

Figure 2C:
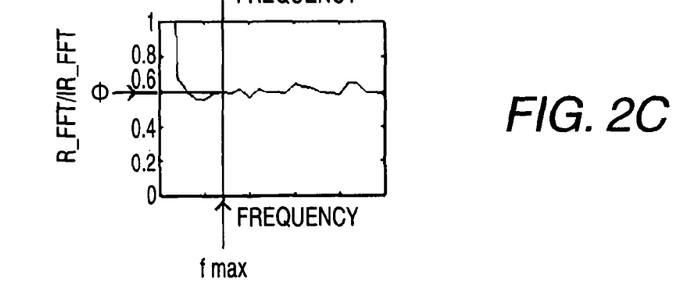
FIG. 2C is a graph showing a ratio between amplitudes of the spectra shown in FIG. 2B.

FIG. 2C shows a ratio between the amplitudes of the spectra shown in FIG. 2B ($R\_FFT(f)/IR\_FFT(f)$). This ratio represents an attenuation ratio $\Phi$ at each frequency of the spectra. Thus, the attenuation ratio $\Phi$ can be expressed by $\Phi(f)=R\_FFT(f)/IR\_FFT(f)$.

When the frequency resolution of FFT is 0.1 Hz, $\Phi(f)$ is computed by separating the pulse wave into frequencies at intervals of 0.1 Hz.

FIGS. 2A to 2C illustrate a case where no noise are superimposed on the pulse wave. However, in the case of actually measured pulse wave, the attenuation ratio $\Phi$ includes $\Phi s$ which corresponds to the attenuation changes in arterial blood, and $\Phi n$ which corresponds to the attenuation changes of noise.

In a first embodiment of the invention, the attenuation ratios $\Phi$ are calculated for a plurality of frequencies, and the attenuation ratio $\Phi$ at a frequency fmax, at which the amplitude of each of the spectra becomes maximum, is set to be the attenuation ratio $\Phi s$ of arterial blood.

Figure 3A:
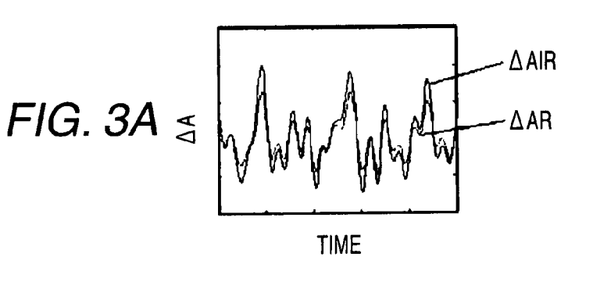
FIG. 3A is a graph showing attenuation change signals obtained from pulse wave signals pulse wave signals measured by the pulse oximeter, in a case where noise is superimposed thereon.
Figure 3B:
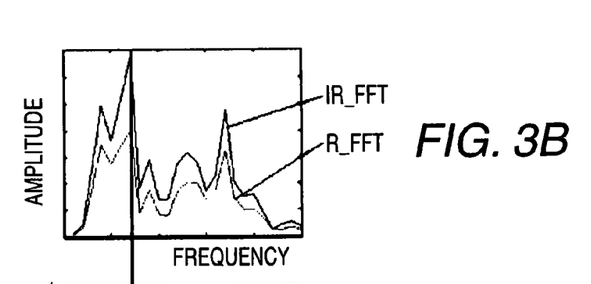
FIG. 3B is a graph showing amplitude spectra obtained by applying a FFT processing with respect to the pulse wave signals shown in FIG. 3A.
Figure 3C:
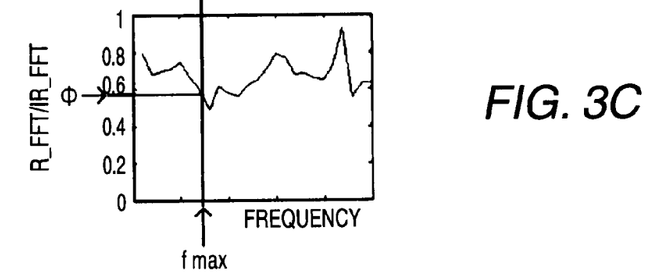
FIG. 3C is a graph showing a ratio between amplitudes of the spectra shown in FIG. 3B, for explaining a signal processing according to a first embodiment of the invention.

FIGS. 3A to 3C respectively correspond to FIGS. 2A to 2C and are showing a case where noise is superimposed on the pulse wave signals.

In comparison with the waveforms shown in FIG. 2B, it is apparent that, in FIG. 3B, peaks due to the noise appear at frequencies other than the frequency of the pulse wave.

In a case where the amplitude due to the noise is relatively smaller than the amplitude of the pulse wave signal (e.g., in a case where the ratio of the amplitude due to the noise to the amplitude of the pulse wave signal is no greater than 0.7, preferably, no greater than 0.5), the attenuation ratio $\Phi$ at the frequency, at which each of the amplitude spectra shows a maximum value, is read and is determined to be the attenuation ratio $\Phi s$ of arterial blood as shown in FIG. 3C. Thus, the attenuation ratio $\Phi s$ of arterial blood can easily be obtained.

In a second embodiment of the invention, the attenuation ratios $\Phi$ are calculated for a plurality of frequencies, and a minimum value of the attenuation ratios $\Phi$ is set to be the attenuation ratio $\Phi s$ of arterial blood.

Generally, the attenuation ratio $\Phi n$ in the frequency, at which the amplitude due to noise appears, tends to be higher than the attenuation ratio $\Phi s$ in the frequency at which the amplitude due to the pulse wave appears.

Figure 3D:
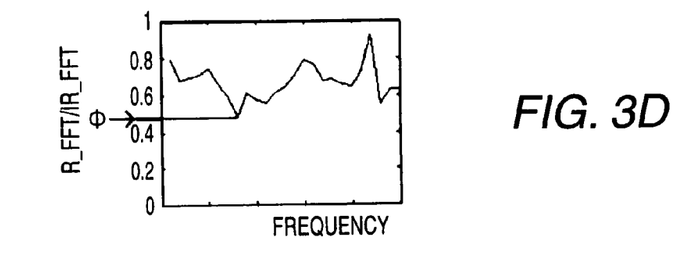
FIG. 3D is a graph showing the ratio between amplitudes of the spectra shown in FIG. 3B, for explaining a signal processing according to a second embodiment of the invention.

This is because of the fact that the change in the attenuation ratio, which is caused by the noise, results mainly from change in the thickness of venous blood. Because the oxygen saturation in venous blood is lower than that of arterial blood, the attenuation ratio On due to the change in thickness of venous blood is lower than the attenuation ratio $\Phi s$. Therefore, the minimum value of the attenuation ratios $\Phi$ can be read as the attenuation ratio $\Phi s$ of arterial blood. FIG. 3D shows this processing.

It is apparent that the ratio $\Phi s$ obtained by this processing is almost the same as that obtained by the processing illustrated in FIG. 3C. Here, the ratio $\Phi s$ obtained by this processing may be taken into account of the judgment performed in the first embodiment.

In a case where the frequency, at which the amplitude peak due to the noise appears, overlaps with the frequency, at which the amplitude peak due to the pulse wave appears, the attenuation ratio $\Phi$ obtained at such a frequency becomes lower than the actual attenuation ratio $\Phi s$ of arterial blood. Thus, the $SpO_2$ cannot correctly be measured when the attenuation ratio $\Phi$ obtained at the above frequency is employed. In such a case, a second-minimum attenuation ratio $\Phi$ obtained at a frequency other than the above frequency may be regarded as that $\Phi s$ of arterial blood.

Figure 7A:
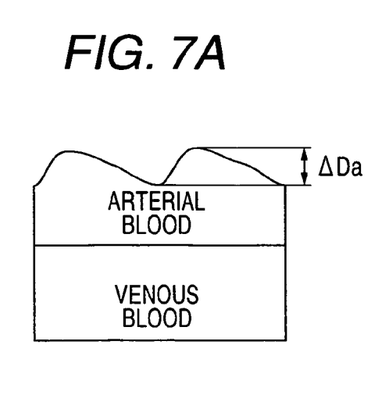
FIG. 7A is a diagram showing a blood pulsation model in a case where no body movement is present.

Next, grounds for the above determination will be described below by using a model in which arterial blood pulsates and increases in thickness when no body movement is present with reference to FIG. 7A, and in which the thickness of arterial blood and that of venous blood simultaneously change when a body movement is present with reference to FIG. 7B.

In the case illustrated in FIG. 7A, the attenuation change $\Delta A$ is measured according to Lambert-Beer's law as follows.

$$\Delta A = \Delta Aa = Ea \cdot Hb \cdot \Delta Da$$

where Aa designates an attenuation change caused by change in the thickness of arterial blood; Ea designates an absorption coefficient of arterial blood (dL/g/cm); Hb denotes a hemoglobin concentration (g/dL); and $\Delta Da$ designates change in the thickness of arterial blood (cm). The attenuation ratio $\Phi$ to be measured is given by the following equation.

$$\Phi = \Delta A_1 / \Delta A_2 = (Ea_1 \cdot Hb \cdot \Delta Da) / (Ea_2 \cdot Hb \cdot \Delta Da) = Ea_1 / Ea_2$$

where the suffixes designate wavelength numbers, and the suffix 1 corresponds to a wavelength of 660 nm, and the suffix 2 corresponds to a wavelength of 940 nm.

The attenuation ratio $\Phi m$ to be measured in the case, in which no body movement is present, is given by the following equation.

$$\Phi m = \Delta A_1 / \Delta A_2 = \Delta A_{a1} / \Delta A_{a2}$$

Thus, the measured $\Phi m$ is the attenuation ratio $\Phi a$ of arterial blood, that is, $\Phi a = \Delta A_{a1} / \Delta A_{a2}$.

Figure 7B:
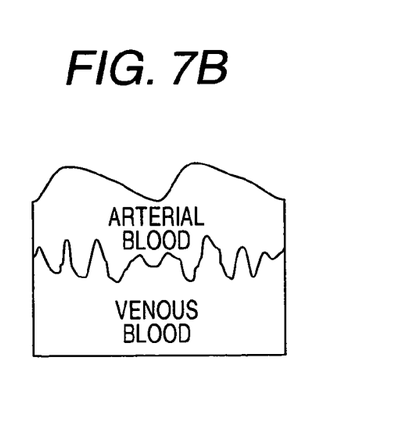
FIG. 7B is a diagram showing the blood pulsation model in a case where a body movement is present.

On the other hand, in the case where a body movement is present, not only the thickness of arterial blood but the thickness of venous blood changes, as shown in FIG. 7B. The attenuation change $\Delta A$ caused in this case is a sum of the attenuation change $\Delta Aa$, which is caused by change in the thickness of arterial blood, and the attenuation change $\Delta Av$, which is caused by change in the thickness of venous blood (i.e., $\Delta A = \Delta Aa + \Delta Av$). The attenuation ratio $\Phi m$ to be measured in this case is given by the following equation.

$$\Phi m = \Delta A_1 / \Delta A_2 = (\Delta A_{a1} + \Delta A_{v1}) / (\Delta A_{a2} + \Delta A_{v2})$$

The attenuation changes are given in the following equations expressed in vector notation below.

$$Aa = (\Delta A_{a2}, \Delta A_{a1})$$

$$Av = (\Delta A_{v2}, \Delta A_{v1})$$

$$Am = (\Delta A_{a2} + \Delta A_{v2}, \Delta A_{a1} + \Delta A_{v1})$$

Figure 8:
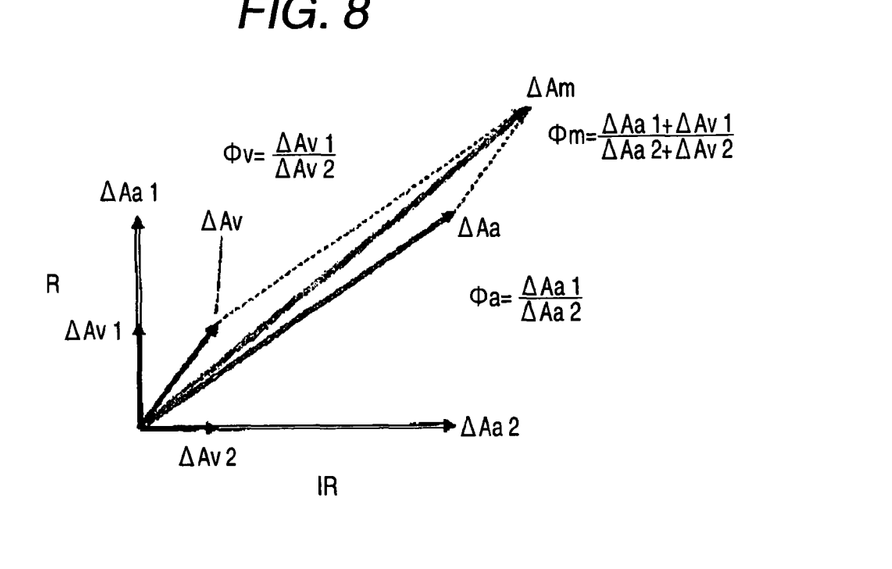
FIG. 8 is a diagram showing a vector representation of attenuation ratios derived from the model shown in FIG. 7B.

The attenuation ratios $\Phi$ corresponding to the above attenuation changes are represented by the respective gradients of the vectors shown in FIG. 8.

Figure 9:
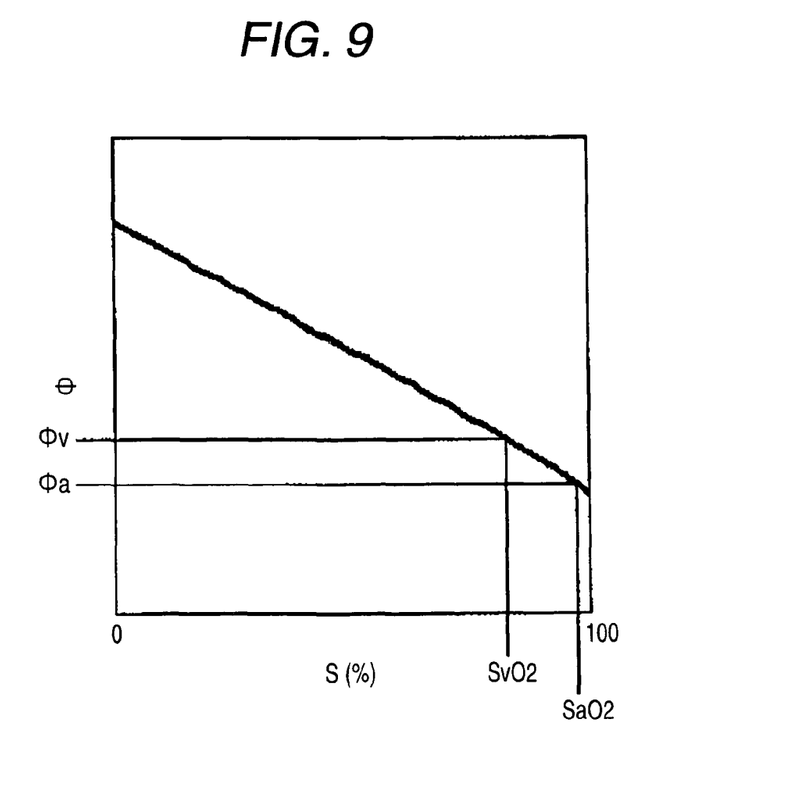
FIG. 9 is a diagram showing a correlation between the attenuation ratio and an oxygen saturation in blood.

Incidentally, oxygen contained in arterial blood is taken into the tissue. Thus, the oxygen saturation Sv in venous blood is lower than that Sa in arterial blood (Sa>Sv). However, because of the correlation between the attenuation ratio $\Phi$ and the oxygen saturation S of blood as shown in FIG. 9, the inequality $\Phi a < \Phi v$ holds.

Therefore, as shown in FIG. 8, the measured attenuation ratio vector Am appears between the vector Aa, whose gradient is small, and the vector Av whose gradient is large. The gradient $\Phi m$ of the measured signal Am is determined by the ratio in length between the vectors Aa and Av on condition that the values of the ratios $\Phi a$ and $\Phi v$ are constant.

In a case where a body movement is small and where the length of the vector Av is nearly equal to 0 ($|Av| \approx 0$), $\Phi m \approx \Phi a$. In a case where a body movement is large and where the length of the vector Av is much larger than that of the vector Aa ($|Av| >> |Aa|$), $\Phi m \approx \Phi v$.

In a case where the attenuation change ratio $\Phi m$ is observed by separating the pulse wave into a plurality of frequencies, the ratio $\Phi$ obtained at the frequency, at which the value of the ratio cm is minimum, has a value closest to the attenuation ratio $\Phi a$ of arterial blood.

The condition for minimizing the ratio $\Phi m$ is that the ratio ($|Aa|/|Av|$) is maximum. However, the length $|Aa|$ is maximum at the fundamental frequency of the pulse wave, among the plurality of frequencies. Thus, assuming that the noise is random like white noise, the ratio ($|Aa|/|Av|$) is maximum at the fundamental frequency of the pulse wave.

Consequently, on condition that the noise is random, the fundamental frequency of the pulse wave can be determined by searching for a frequency at which the ratio $\Phi m$ is minimum.

Figure 10A:
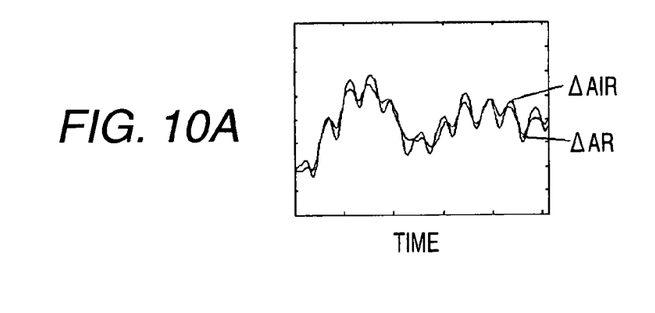
FIG. 10A is a graph showing attenuation change signals obtained from pulse wave signals pulse wave signals measured by the pulse oximeter, in a case where noise is superimposed thereon.
Figure 10B:
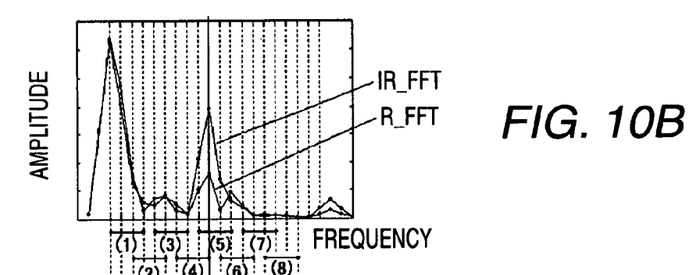
FIG. 10B is a graph showing amplitude spectra obtained by applying a FFT processing with respect to the pulse wave signals shown in FIG. 10A, for explaining a third embodiment of the invention.

Next, a third embodiment of the Invention will be described. FIGS. 10A and 10B respectively correspond to FIGS. 3A and 3B. In this embodiment, an effective frequency band (e.g., from 0.5 Hz to 5.0 Hz) of each of the amplitude spectra is divided into a plurality of frequency bands (e.g., eight bands) each of which has a plurality of measurement points (e.g., four points) denoted by dashed lines in FIG. 10B.

In this embodiment, the divided frequency bands arranged such that parts of adjacent divided frequency bands are overlapped to each other. However, the adjacent divided frequency bands may not be overlapped to each other.

Figure 10C:
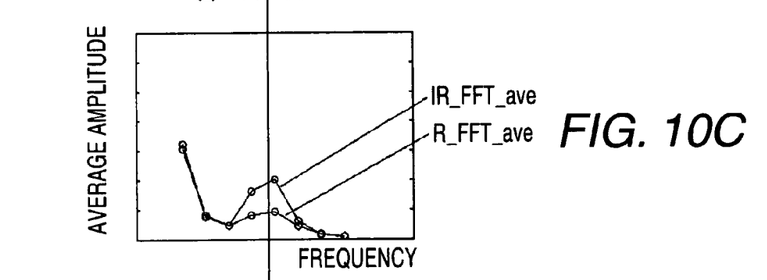
FIG. 10C is a graph showing values each of which is an average value of amplitudes in each of divided frequency bands shown in FIG. 10B.

Next, as shown in FIG. 10C, an average value of the amplitudes at the plural measurement points is calculated for each of the divided frequency bands. The average value calculated for the spectrum corresponding to the red light R is denoted as R_FFT_ave. The average value calculated for the spectrum corresponding to the infrared light IR is denoted as IR_FFT_ave.

Figure 10D:
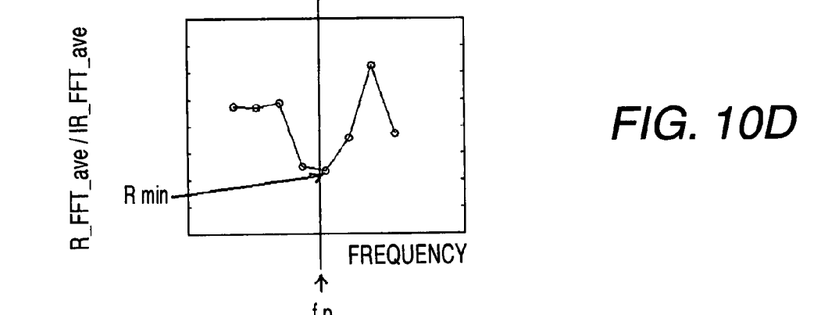
FIG. 10D is a graph showing values each of which is a ratio between the average values shown in FIG. 10C in each of the divided frequency bands.

Further, as shown in FIG. 10D, a ratio between the thus calculated average values (R_FFT_ave/IR_FFT_ave) is calculated for each of the divided frequency bands.

Finally, the minimum value Rmin of the thus calculated ratios is regarded as an attenuation ratio in arterial blood, and the frequency associated with the minimum value is regarded as a fundamental frequency fp of the pulse wave.

In this embodiment, the average value of the amplitudes at the plural measurement points is first calculated for each of the divided frequency bands, and the ratio between the average values is then calculated as the attenuation ratio. However, a ratio between the amplitudes for each of the measurement points may be first calculated as an attenuation ratio, and an average value of the thus calculated ratios may be then calculated for each of the divided frequency bands.

In addition, the following processing may be adopted. It is determined whether a maximal point of the amplitude spectrum is included for each of the divided frequency shown in FIG. 10B. A divided frequency band which is judged as one including the maximal point becomes a candidate for a frequency band including an attenuation ratio in arterial blood. Among such candidates, one including the minimum value of the ratio between the average values (R_FFT_ave/IR_FFT_ave) is determined as the frequency band including an attenuation ratio in arterial blood.

The above judgment may be performed at least one of the amplitude spectrum corresponding to the red light R (R_FFT) and the amplitude spectrum corresponding to the infrared light IR (IR_FFT).

A divided frequency band which is judged as one not including the maximal point will not become the candidate even if the ratio of the average values (R_FFT_ave/IR_FFT_ave) of the divided frequency band has a relatively small value.

Specifically, in order to judge whether one divided frequency band has a maximal point of the amplitude spectrum, it is judged an n-th measurement point in the divided frequency band denoted as FFT(n) is the maximal point when the FFT(n) satisfies both of the following inequalities: FFT(n−1)<FFT(n) and FFT(n)>FFT(n+1).

However, if the n-th measurement point judged as the maximal point is located at one of both ends of one of the divided frequency bands (2) through (7) shown in FIG. 10B, the frequency band including such an n-th measurement point will not be regarded as one including the maximal point This is because both ends of one of these divided frequency bands is contained in an adjacent one of the divided frequency bands. In other words, since the measurement points corresponding to the minimum frequency in the divided frequency band (1) and the maximum frequency in the divided frequency band (8) are not contained in another divided frequency band, if these measurement points are judged as the maximal point, the judgment is made valid.

The above judgment in connection with the maximal point may be executed after the execution of the processings shown in FIGS. 10A to 10D in order to enhance the accuracy of the determination of the attenuation ratio in arterial blood based on the minimum value Rmin.

In a case where the amplitude of the noise is relatively smaller than the amplitude of the pulse wave, the attenuation ratio Φ at the frequency, at which the amplitude spectrum shows a maximum value, can be read and is determined to be the attenuation ratio Φs of arterial blood. However, in a case where the amplitude of the noise is somewhat large, it is difficult to find out a peak corresponding to the pulse wave from the amplitude spectrum obtained by the FFT or the like.

Figure 4A:
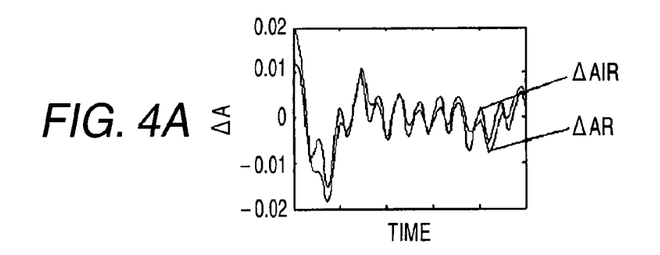
FIG. 4A is a graph showing attenuation change signals obtained from pulse wave signals measured by the pulse oximeter, in a case where large noise is superimposed.
Figure 4B:
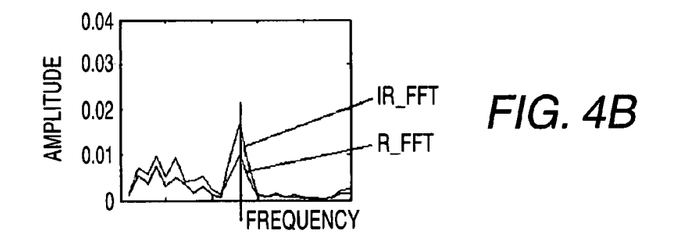
FIG. 4B is a graph showing amplitude spectra obtained by applying a FFT processing with respect to the pulse wave signals shown in FIG. 4A.

FIGS. 4A and 4B respectively correspond to FIGS. 2A and 2B and are showing a case where large noise is superimposed on the pulse wave signals. The amplitude of the noise is almost the same as the amplitude of the pulse wave signal. Although the pulse wave can be still recognized in FIG. 4A, and the peak corresponding to the pulse wave can be recognized in FIG. 4B, in a case where a plurality of peaks having similar amplitudes, it is difficult to identify the peak corresponding to the pulse wave.

Figure 4C:
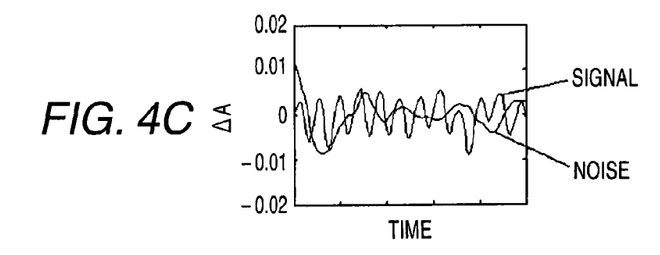
FIG. 4C is a graph showing attenuation change signals obtained from pulse wave signals measured by the pulse oximeter, in a case where a signal separation method is applied.
Figure 4D:
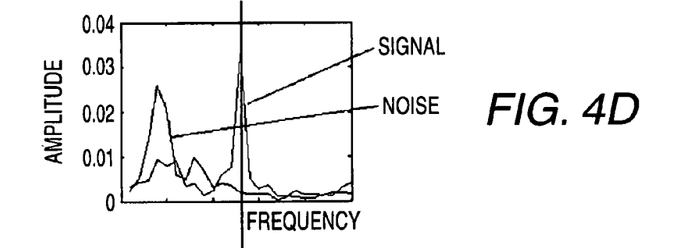
FIG. 4D is a graph showing amplitude spectra obtained by applying a FFT processing with respect to the pulse wave signals shown in FIG. 4C.

In such a case, a well-known signal separation method may be applied before the FFT processing is performed. As shown in FIG. 4C, the pulse wave signal and the noise can clearly be separated from each other. After the FFT processing is performed with respect to the thus separated signals, the frequency of the pulse wave can clearly be determined in the spectra as shown in FIG. 4D.

Figure 4E:
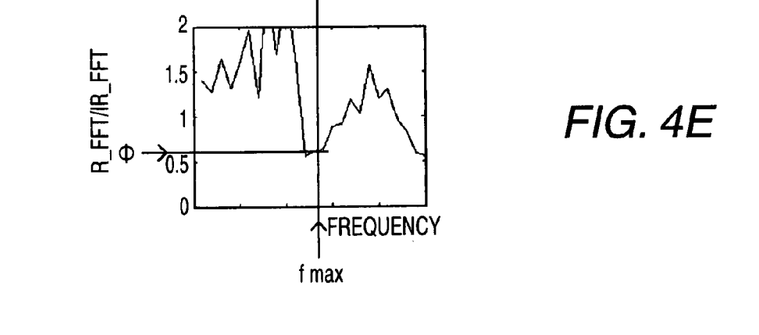
FIG. 4E is a graph showing a ratio between amplitudes of the spectra shown in FIG. 4D.

The attenuation ratio Φ of the arterial blood can be determined as well as the first or second embodiment as shown in FIG. 4E.

Figure 5A:
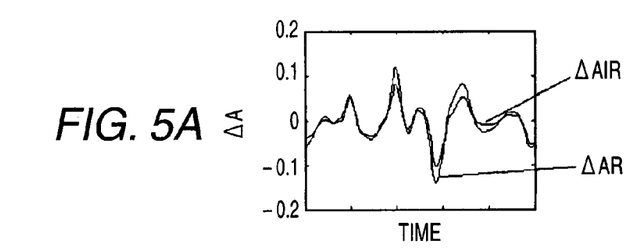
FIG. 5A is a graph showing attenuation change signals obtained from pulse wave signals measured by the pulse oximeter, in a case where extreme large noise is superimposed.
Figure 5B:
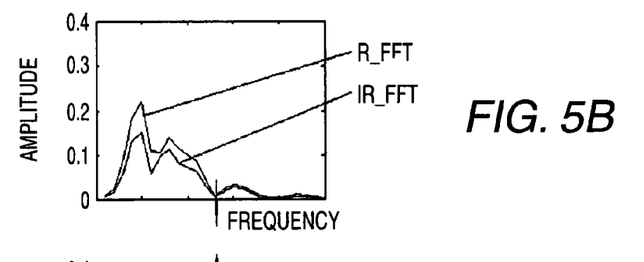
FIG. 5B is a graph showing amplitude spectra obtained by applying a FFT processing with respect to the pulse wave signals shown in FIG. 5A.

FIGS. 5A to 5E respectively correspond to FIGS. 4A to 4E and are showing a case where extreme large noise is superimposed on the pulse wave signals. The amplitude of the noise is about ten times the amplitude of the pulse wave signal. As shown in FIGS. 5A and 5B, it is impossible to recognize pulse wave components from the measured waveforms and the amplitude spectra. During such a vigorous body movement, arterial blood is often moved due to the body movement. Thus, even if the signal separation method is applied, the obtained waveform of the signal shown in FIG. 6C entirely differs from the pulse wave.

Figure 5C:
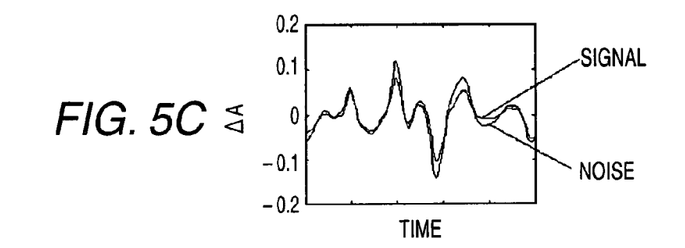
FIG. 5C is a graph showing attenuation change signals obtained from pulse wave signals measured by the pulse oximeter, in a case where a signal separation method is applied.
Figure 5D:
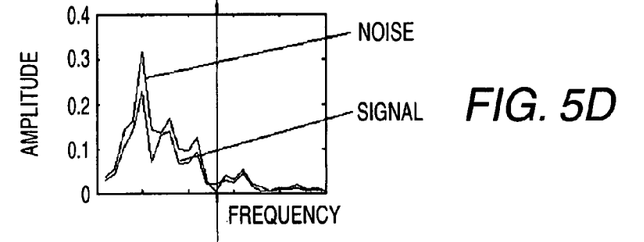
FIG. 5D is a graph showing amplitude spectra obtained by applying a FFT processing with respect to the pulse wave signals shown in FIG. 5C.

Therefore, even when the movement of an arterial blood component corresponding to the signal can be separated from the movement of a venous blood component corresponding to the noise, the frequency of each of the pulse waves cannot be identified according to the waveforms shown in FIG. 5C and the those obtained after the FFT processing, which are shown in FIG. 5D.

Figure 5E:
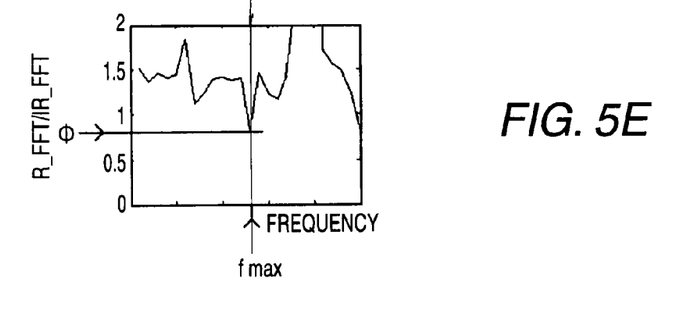
FIG. 5E is a graph showing a ratio between amplitudes of the spectra shown in FIG. 5D.

In a case where the amplitude corresponding to the noise is larger than the amplitude of the pulse wave signal, it is difficult to calculate a pulse rate and an oxygen saturation by employing a frequency, at which the amplitude of the spectrum is maximum, as the fundamental frequency of the pulse wave. However, according to the method as explained in the second and third embodiments, the frequency of a pulse wave can be determined by searching a frequency, at which the attenuation ratio is minimum, as shown in FIG. 5E. The attenuation ratio at the determined frequency can be obtained as the oxygen saturation in arterial blood.

In a case where no noise is superimposed on the pulse wave, a maximum amplitude appears at the fundamental frequency of the pulse wave, and higher harmonic waves appear at frequencies which are twice and three times the fundamental frequency as shown in FIG. 2B. In a case where a large noise is superimposed on the pulse wave, frequencies, at each of which a peak amplitude is present, is not distributed in a narrow band, but is distributed in a wide band as shown in FIG. 5B. In a case where the amplitudes corresponding to noise are distributed in a narrow band, as shown in FIG. 3B, a peak appears at a frequency that differs from the fundamental frequency and from the frequencies of the higher harmonic waves.

In view of the above, the pulse oximeter may comprise a selector operable to select a frequency, at which the attenuation ratio is minimum, as a frequency representing an oxygen saturation in arterial blood, in a case where the frequency corresponding to the second-highest peak obtained by FFT is not twice the fundamental frequency that is the highest peak, or where the half-value width of the first peak obtained by FFT is neither equal to nor less than a prescribed value.

Figure 6:
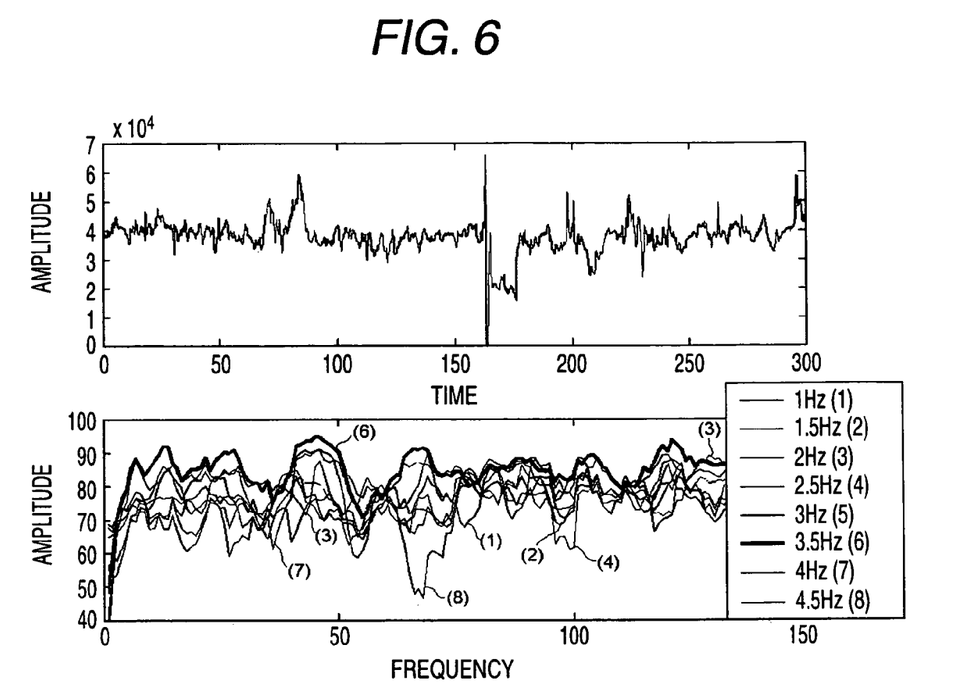
FIG. 6 is a graph showing an actual measurement example.

FIG. 6 shows an example in which a pulse wave, the SpO2 of which cannot be calculated by the conventional method because of the large noise, is divided into 8 frequency bands such that each of the bands has a band width of 1 Hz and center frequencies are ranged from 1.0 Hz to 4.5 Hz at a fixed interval of 0.5 Hz, and $SpO_2$ is calculated for each of the divided bands. It is apparent that different values of $SpO_2$ corresponding to different attenuation ratios are obtained by the above measurement. Since arterial blood exhibits a higher oxygen saturation than venous blood, the $SpO_2$ of the band, which exhibits a highest value of the oxygen saturation, can be regarded as the oxygen saturation of arterial blood. Further, a representative frequency (e.g., a center frequency) of the frequency band including the highest value in the oxygen saturation can be regarded as the frequency of the pulse wave.

In the conventional method, the pulse wave signal and the noise are separated on the basis of the attenuation ratio. That is, in order to separate a pulse wave signal and noise at an analysis section of interest, it is necessary to input an attenuation ratio which is obtained in a previous section (i.e., data in the past is necessary). On the other hand, according to the method of the invention, since it is not necessary to refer data in the past, processing speed can be enhanced.

Although the present invention has been shown and described with reference to specific embodiments, various changes and modifications will be apparent to those skilled in the art from the teachings herein. Such changes and modifications as are obvious are deemed to come within the spirit, scope and contemplation of the invention as defined in the appended claims.

For example, in the above embodiments, the pulse wave is separated into a plurality of frequencies by the FFT. However, a plurality of bandpass filters, whose central frequencies differ from one another, may be used for separating the pulse wave into a plurality of frequencies.

The oxygen saturation measuring apparatus and method of the invention described in the appended claims 1 to 12 can realize a signal processing method enabled to alleviate a burden of calculation for extracting a common signal component by processing two signals of the same kind, which are substantially simultaneously extracted from a same medium. Also, the concentration of an object material can be measured with good accuracy by applying the signal processing method even when a noise due to the body movement of the medium is generated in a pulse wave signal. Also, even when a noise due to the body movement is generated in a pulse wave data signal, a pulse rate can be obtained with good precision by removing a noise from a pulse wave signal.

What is claimed is:

1. An apparatus for measuring an oxygen saturation in blood, comprising:
   a plurality of light emitters, adapted to irradiate a living tissue with a plurality of light beams having different wavelengths;
   a light receiver, adapted to receive the light beams reflected from or transmitted through the living tissue to generate pulse wave signals in accordance with pulsations of the blood in the living tissue;
   a separator, operable to separate each of the pulse wave signals into a plurality of amplitude signals each of which is associated with one frequency, thereby generating pairs of amplitude signals each of which is associated with one of a plurality of frequencies;
   a first processor, operable to calculate a ratio between the amplitude signals in each of the pairs of the amplitude signals;
   a selector, which is operable to select one of the pairs of the amplitude signals based on the amplitude values of the amplitude signals, wherein the selector selects a pair of the amplitude signals that have maximum amplitude values; and
   a second processor, operable to calculate the oxygen saturation based on the ratio of the selected one of the pairs of the amplitude signals.

2. The apparatus as set forth in claim 1, wherein:
   the separator comprises either an FFT processor or a digital filter.

3. The apparatus as set forth in claim 1, wherein:
   the selector is operable to select either such a pair of the amplitude signals that have maximum amplitude values or such a pair of the amplitude signals that the ratio takes a minimum value in accordance with a prescribed condition.

4. The apparatus as set forth in claim 3, wherein:
   the prescribed condition includes a waveform of the amplitude signals.

5. The apparatus as set forth in claim 1, wherein the light beams include a red light beam and an infrared light beam.

6. A method for measuring an oxygen saturation in blood, comprising:
   irradiating a living tissue with a plurality of light beams having different wavelengths;
   receiving the light beams reflected from or transmitted through the living tissue to generate pulse wave signals in accordance with pulsations of the blood in the living tissue;
   separating each of the pulse wave signals into a plurality of amplitude signals each of which is associated with one frequency, thereby generating pairs of amplitude signals each of which is associated with one of a plurality of frequencies;
   calculating a ratio between the amplitude signals in each of the pairs of the amplitude signals;
   selecting one of the pairs of the amplitude signals based on the amplitude values of the amplitude signals; and
   calculating the oxygen saturation based on the ratio of the selected one of the pairs of the amplitude signals,
   wherein a pair of the amplitude signals that have maximum amplitude values is selected as the selected one of the pairs of the amplitude signals.

7. The method as set forth in claim 6, wherein:
   the separating is performed with either an FFT processing or a digital filtering.

8. The method as set forth in claim 6, wherein:
   either such a pair of the amplitude signals that have maximum amplitude values or such a pair of the amplitude signals that the ratio takes a minimum value is selected as the one of the pairs of the amplitude signals in accordance with a prescribed condition.

9. The method as set forth in claim 8, wherein:
   the prescribed condition includes a waveform of the amplitude signals.

10. An apparatus for measuring an oxygen saturation in blood, comprising:
    a plurality of light emitters, adapted to irradiate a living tissue with a plurality of light beams having different wavelengths;

a light receiver, adapted to receive the light beams reflected from or transmitted through the living tissue to generate pulse wave signals in accordance with pulsations of the blood in the living tissue;

a separator, operable to separate each of the pulse wave signals into a plurality of amplitude signals each of which is associated with one frequency, thereby generating pairs of amplitude signals each of which is associated with one of a plurality of frequencies;

a first processor, operable to calculate a ratio between the amplitude signals in each of the pairs of the amplitude signals;

a selector, which is operable to select one of the pairs of the amplitude signals based on the amplitude values of the amplitude signals, wherein the selector selects a pair of the amplitude signals that the ratio between the amplitude signales takes a minimum value; and a second processor, operable to calculate the oxygen saturation based on the ratio of the selected one of the pairs of the amplitude signals.

11. The apparatus as set forth in claim 10, wherein:
the first processor comprises:
a first calculator, operable to define a plurality of frequency bands each of which includes a plurality of amplitude signals obtained from each of the pulse wave signals, and operable to calculate an average value of the amplitude signals in each of the frequency bands, thereby generating pairs of average values each of which is associated with one of the frequency bands; and
a second calculator, operable to calculate an average ratio between the average values in each of the pairs of the average values; and
the selector is operable to select such a frequency band that the average ratio takes a minimum value.

12. The apparatus as set forth in claim 11, wherein:
a part of one of the frequency bands is overlapped with a part of another one of the frequency bands.

13. The apparatus as set forth in claim 10, wherein:
the first processor comprises:
a first calculator, operable to:
define a plurality of frequency bands each of which includes a plurality of amplitude signals obtained from each of the pulse wave signals;
judge whether there is a maximal point of the amplitude signals in each of the frequency bands; and
calculate an average value of the amplitude signals in at least one of the frequency bands which is judged as one including the maximal point, thereby at least one pair of average values each of which is associated with one of the frequency bands; and
a second calculator, operable to calculate an average ratio between the average values in each of the at least one pair of the average values; and
the selector is operable to select such a frequency band that the average ratio takes a minimum value.

14. The apparatus as set forth in claim 13, wherein:
a part of one of the frequency bands is overlapped with a part of another one of the frequency bands.

15. The apparatus as set forth in 10, wherein:
the first processor comprises:
a first calculator, operable to calculate ratios each of which is a ratio between each of the pairs of the amplitude signals; and
a second calculator, operable to define a plurality of frequency bands each of which includes a plurality of amplitude signals obtained from each of the pulse wave signals, and operable to calculate an average value of the ratios in each of the frequency bands, thereby generating a plurality of average values; and
the selector is operable to select such a frequency band that the average value takes a minimum value.

16. The apparatus as set forth in claim 15, wherein:
a part of one of the frequency bands is overlapped with a part of another one of the frequency bands.

17. A method for measuring an oxygen saturation in blood, comprising:
irradiating a living tissue with a plurality of light beams having different wavelengths;
receiving the light beams reflected from or transmitted through the living tissue to generate pulse wave signals in accordance with pulsations of the blood in the living tissue;
separating each of the pulse wave signals into a plurality of amplitude signals each of which is associated with one frequency, thereby generating pairs of amplitude signals each of which is associated with one of a plurality of frequencies;
calculating a ratio between the amplitude signals in each of the pairs of the amplitude signals;
selecting one of the pairs of the amplitude signals based on the amplitude values of the amplitude signals; and
calculating the oxygen saturation based on the ratio of the selected one of the pairs of the amplitude signals,
wherein a pair of the amplitude signals that the ratio takes a minimum value is selected as the selected one of the pairs of the amplitude signals.

18. The method as set forth in claim 17, further comprising:
defining a plurality of frequency bands each of which includes a plurality of amplitude signals obtained from each of the pulse wave signals;
calculating an average value of the amplitude signals in each of the frequency bands, thereby generating pairs of average values each of which is associated with one of the frequency bands;
calculating an average ratio between the average values in each of the pairs of the average values; and
selecting such a frequency band that the average ratio takes a minimum value.

19. The method as set forth in claim 18, wherein:
a part of one of the frequency bands is overlapped with a part of another one of the frequency bands.

20. The method as set forth in claim 17, further comprising:
defining a plurality of frequency bands each of which includes a plurality of amplitude signals obtained from each of the pulse wave signals;
judging whether there is a maximal point of the amplitude signals in each of the frequency bands;
calculating an average value of the amplitude signals in at least one of the frequency bands which is judged as one including the maximal point, thereby at least one pair of average values each of which is associated with one of the frequency bands;
calculating an average ratio between the average values in each of the at least one pair of the average values; and
selecting such a frequency band that the average ratio takes a minimum value.

21. The method as set forth in claim 20, wherein:
a part of one of the frequency bands is overlapped with a part of another one of the frequency bands.

22. The method as set forth in claim 17; further comprising:
calculating ratios each of which is a ratio between each of the pairs of the amplitude signals;

defining a plurality of frequency bands each of which includes a plurality of amplitude signals obtained from each of the pulse wave signals;

calculating an average value of the ratios in each of the frequency bands, thereby generating a plurality of average values; and selecting such a frequency band that the average value takes a minimum value.

23. The method as set forth in claim 22, wherein:

a part of one of the frequency bands is overlapped with a part of another one of the frequency bands.

24. An apparatus for measuring an oxygen saturation in blood, comprising:

a plurality of light emitters, adapted to irradiate a living tissue with a plurality of light beams having different wavelengths;

a light receiver, adapted to receive the light beams reflected from or transmitted through the living tissue to generate pulse wave signals in accordance with pulsations of the blood in the living tissue;

a separator, operable to separate each of the pulse wave signals into a plurality of amplitude signals each of which is associated with one frequency, thereby generating pairs of amplitude signals each of which is associated with one of a plurality of frequencies;

a first processor, operable to calculate a ratio between the amplitude signals in each of the pairs of the amplitude signals;

a selector, which is operable to select one of the pairs of the amplitude signals based on the amplitude values of the amplitude signals, wherein the selector selects either a pair of the amplitude signals that have maximum amplitude values or a pair of the amplitude signals that the ratio takes a minimum value in accordance with a prescribed condition; and a second processor, operable to calculate the oxygen saturation based on the ratio of the selected one of the pairs of the amplitude signals.

25. A method for measuring an oxygen saturation in blood, comprising:

irradiating a living tissue with a plurality of light beams having different wavelengths;

receiving the light beams reflected from or transmitted through the living tissue to generate pulse wave signals in accordance with pulsations of the blood in the living tissue;

separating each of the pulse wave signals into a plurality of amplitude signals each of which is associated with one frequency, thereby generating pairs of amplitude signals each of which is associated with one of a plurality of frequencies;

calculating a ratio between the amplitude signals in each of the pairs of the amplitude signals;

selecting one of the pairs of the amplitude signals based on the amplitude values of the amplitude signals; and calculating the oxygen saturation based on the ratio of the selected one of the pairs of the amplitude signals, wherein either a pair of the amplitude signals that have maximum amplitude values or a pair of the amplitude signals that the ratio takes a minimum value is selected as the selected one of the pairs of the amplitude signals in accordance with a prescribed condition.

* * * * *